United States Patent [19]

Träubel et al.

[11] Patent Number: 5,554,711

[45] Date of Patent: Sep. 10, 1996

[54] POLYISOCYANATE ADDITION COMPOUNDS CONTAINING CYANAMIDE GROUPS AND THEIR USE

[75] Inventors: Harro Träubel, Leverkusen; Thomas Münzmay, Dormagen; Tillmann Hassel, Köln; Wilhelm Krümmel; Hans-Albert Ehlert, both of Leverkusen; Joachim Kochta, Bonn, all of Germany

[73] Assignee: Bayer Aktiengesellschaft, Leverkusen, Germany

[21] Appl. No.: 301,742

[22] Filed: Sep. 6, 1994

[30] Foreign Application Priority Data

Sep. 8, 1993 [DE] Germany ............... 43 30 378.1

[51] Int. Cl.⁶ .................................................. C08G 18/30
[52] U.S. Cl. .................. 528/49; 528/71; 528/73; 528/367; 528/368; 252/182.23; 560/25; 560/115; 560/158; 544/67; 548/951; 540/356; 525/452
[58] Field of Search ............... 528/49, 71, 73, 528/74.5, 367, 368; 252/182.23; 560/25, 115, 158; 544/67; 548/951; 540/356; 525/452

[56] References Cited

U.S. PATENT DOCUMENTS

| 4,106,897 | 8/1978  | Träubel et al. ............ 8/94.33 |
| 4,619,966 | 10/1986 | Schäfer et al. ............ 524/589 |
| 4,647,647 | 3/1987  | Haubennestel ............ 528/83  |
| 4,707,386 | 11/1987 | Schäfer et al. ............ 427/386 |
| 4,895,921 | 1/1990  | Schäfer et al. ............ 528/45  |
| 4,918,135 | 4/1990  | Probst et al. ............ 524/714 |
| 5,284,928 | 2/1994  | Münzmay et al. ............ 528/52 |

Primary Examiner—Rachel Johnson
Attorney, Agent, or Firm—Joseph C. Gil; Richard E. L. Henderson

[57] ABSTRACT

The invention relates to reaction products prepared from (a) organic polyisocyanates, (b) 0.005 to 0.9 equivalents of a $C_{6-24}$ alcohol per equivalent of NCO or latent NCO present in component (a), (c) 0.1 to 0.995 mol of cyanamide per equivalent of NCO or latent NCO present in component (a), and (d) ammonia or a volatile amine as neutralizing agent for the cyanamide groups of component (c), with the proviso that the reaction products are free from polyester and polyether groups and from halogen atoms.

5 Claims, No Drawings

POLYISOCYANATE ADDITION COMPOUNDS CONTAINING CYANAMIDE GROUPS AND THEIR USE

BACKGROUND OF THE INVENTION

This invention relates to reaction products of organic polyisocyanates, long-chain alcohols, cyanamide, and ammonia or a volatile amine as neutralizing agent for the cyanamide groups in which the reaction products are free from polyester and polyether groups and halogen atoms.

The suitability of anionically modified polyisocyanate products for the preparation of aqueous dispersions rests on the presence of incorporated ionic centers, more particularly incorporated sulfonate or carboxylate groups. In the preparation of coatings from such dispersions, the ionic centers generally remain in the resultant coatings, resulting in a reduction in the resistance to water of the resulting coating.

In addition, water-dispersible polyisocyanate addition products modified by anionic cyanourea groups are known. Cf. German Offenlegungsschriften 3,441,934, 3,600,595, 3,735,198, 3,813,840, and 4,133,572. Coatings obtained from such dispersions are considerably more resistant to water than coatings obtained from standard PUR dispersions because the hydrophilicizing cyanourea anions acquire a self-crosslinking character after loss of the counterion and thus lose their hydrophilicity on completion of crosslinking.

Resistance to water and a reduction in hydrophilicity inherent in the products is also important in the case of dispersion aids (for example, for paraffins, pigments, polymers).

Whereas tanning agents form chemical bonds with the collagen in leather and are supposed to increase the shrinkage temperature of leather through this crosslinking, so-called retanning materials are auxiliaries that have little or no tanning effect of their own but lead to better dyeability and to greater softness and fullness. Such materials must be capable of penetrating into leather and of dispersing and fixing inter alia oiling agents or vegetable tanning materials therein. Examples of such retanning agents are formaldehyde/naphthalene sulfonic acid condensates, (meth)acrylic acid polymers, (meth)acrylic acid/acrylonitrile copolymers, oligourethanes containing ionic groups (see, for example, U.S. Pat. No. 4,106,897) and dicyanodiamide resins (*JALCA*, 83, 196 (1988)).

It has now surprisingly been found that when the reaction products of this invention are used as retanning materials, very soft leathers characterized by excellent feel are formed, and the reaction products are absorbed into the leather until the bath is substantially quantitatively exhausted. The required fastness values are obtained surprisingly quickly so that the leather can be further processed without unwanted delay. A major advantage of products of this invention is their reaction in the leather to form a water-insoluble (nonhydrophilic) dimer or oligomer. Accordingly, the products of the invention are not washed out and do not migrate to any significant extent on completion of the reaction.

SUMMARY OF THE INVENTION

Accordingly, the present invention relates to reaction products (preferably having (number) average molecular weights of less than 5,000, more preferably 800 to 3,000) of (a) an organic polyisocyanate, (b) 0.005 to 0.9 equivalents of a $C_{6-24}$ (preferably $C_{12-18}$) alcohol per equivalent of NCO or latent NCO present in component (a), (c) 0.1 to 0.995 mol of cyanamide per equivalent of NCO or latent NCO present in component (a), and (d) ammonia or a volatile amine as neutralizing agent for the cyanamide groups of component (c), with the proviso that the reaction products are free from polyester and polyether groups and from halogen atoms.

In the context of the invention, the term "cyanamide groups" includes functional groups of any type containing groups corresponding to the formula

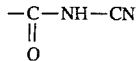

(for example, cyanourea groups of the formula

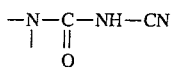

or cyanaminocarbonyl urea groups of the formula

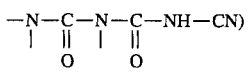

and groups containing salts of these compounds corresponding to the formula

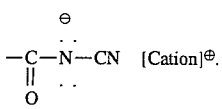

The present invention also relates to a process for the preparation of these products by reaction of components (a) to (d).

DETAILED DESCRIPTION OF THE INVENTION

Organic polyisocyanates (a) suitable for the preparation of the reaction products according to the invention include any organic compounds that contain at least two free isocyanate groups per molecule. Diisocyanates of formula $$X(NCO)^2$$

in which X is a difunctional aliphatic hydrocarbon group containing 4 to 12 carbon atoms, a difunctional cycloaliphatic hydrocarbon group containing 6 to 15 carbon atoms, a difunctional aromatic hydrocarbon group containing 6 to 15 carbon atoms, or a difunctional araliphatic hydrocarbon group containing 7 to 15 carbon atoms, are preferably used.

Examples of preferred diisocyanates are tetramethylene diisocyanate, methyl pentamethylene diisocyanate, hexamethylene diisocyanate ("HDI"), dodecamethylene diisocyanate, 1,4-diisocyanatocyclohexane, 1-isocyanato-3,3,5-trimethyl-5-isocyanatomethylcyclohexane ("isophorone diisocyanate" or "IPDI"), 4,4'-diisocyanatodicyclohexylmethane ("hydrogenated MDI", "HMDI", or "H12-MDI"), 4,4'-diisocyanatodicyclohexyl-2,2-propane, 1,4-diisocyanatobenzene, 2,4- and 2,6-diisocyanatotoluene and mixtures of these isomers ("TDI"), 4,4'-diisocyanatodiphenylmethane, 2,2'- and 2,4'-diisocyanatodiphenylmethane ("MDI"), p-xylylene diisocyanate, p-isopropylidene diisocyanate, and mixtures consisting of these compounds.

The more highly functional polyisocyanates known in polyurethane chemistry or even known modified polyisocyanates (for example, polyisocyanates containing carbodiimide groups, allophanate groups, isocyanurate groups, urethane groups, and/or biuret groups) may, of course, also be used either individually or in admixture. Other suitable polyisocyanates (a) include compounds containing oxadiazinetrione structural units of formula (I) or uretdione structural units of formula (II):

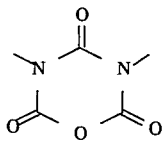
(I)

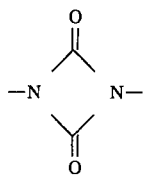
(II)

Suitable synthesis components (a) for introducing the oxadiazinetrione and/or uretdione structural units corresponding to formulas (I) and (II) are diisocyanates corresponding to formula (III) and/or formula (IV):

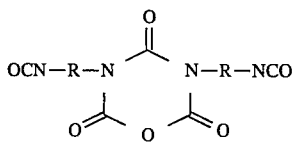
(III)

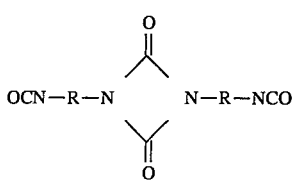
(IV)

in which each R independently represents the difunctional radical of an aliphatic hydrocarbon containing 1 to 15 carbon atoms, a cycloaliphatic hydrocarbon containing 3 to 15 carbon atoms, an araliphatic hydrocarbon containing 7 to 15 carbon atoms, or an aromatic hydrocarbon containing 6 to 12 carbon atoms. Examples of such polyisocyanates (a) are 1,3bis-(5-isocyanato-1,3,3-trimethylcyclohexylmethylene)-2,4-dioxo-1,3diazetidine; 1,3-bis(3-isocyanato-4-methylphenyl)-2,4-dioxo-1,3-diazetidine; 1,3-bis(6-isocyanatohexyl)-2,4-dioxo-1,3-diazetidine; 3,5-bis(5-isocyanato-1,3,3-trimethylcyclohexylmethylene)-2,4,6-trioxotetrahydro-1,3,5-oxadiazine; 3,5-bis(4-isocyanatocyclohexyl)-2,4,6-trioxotetrahydro-1,3,5-oxadiazine, and 3,5-bis(6-isocyanatohexyl)-2,4,6-trioxotetrahydro-1,3,5-oxadiazine (Desmodur® LB 202, a product of Bayer AG).

Of the isocyanates corresponding to formulas (III) and (IV), those of the oxadiazinetrione series (III) are preferably used, with 3,5-bis(6-isocyanatohexyl)-2,4,6-trioxotetrahydro-1,3,5-oxadiazine being particularly preferred.

Because isocyanate groups are lost by reaction with the alcohol, isocyanates containing more than two isocyanate groups are most particularly preferred. Suitable such isocyanates include the isocyanurates, biurets, trisurethanes (and their higher analogs) of TDI, IPDI, MDI, HDI, H12-MDI, 1,4-diisocyanatocyclohexane, prepolymers and the like. By virtue of their better fastness to light, aliphatic isocyanates are again most particularly preferred.

Alcohols (b) suitable for the preparation of the reaction products according to the invention include, for example, alkanols, such as hexanol, octanol, 2-ethylhexanol, lauryl alcohol, cetyl alcohol, and stearyl alcohol; alkenols, such as oleyl alcohol; cycloaliphatic alcohols, such as cyclohexanol and hydroxymethylcyclohexane; and araliphatic alcohols, such as benzyl alcohol.

The cyanamide (c) to be used for the preparation of the reaction products according to the invention is preferably used in the salt form obtained by neutralization with component (d). Cations of volatile amines are preferably used as the cation. Volatile amines (d) include tertiary amines with up to 12 carbon atoms per molecule, such as, for example, triethylamine, trimethylamine, triisopropylamine, tributylamine, N,N-dimethylaminoethanol, tris(isopropanol)amine, pyridine, or N-methyl-morpholine. Ammonia and triethylamine are most particularly preferred components (d).

In general, an intermediate product initially prepared by reaction of components (a) and (b) is allowed to react in water in the presence of cyanamide (c) and neutralizing agent (d) or in the presence of a cyanamide neutralized with component (d) to form the required end product. The reaction temperature for these reactions is generally kept between 20° C. and 80° C. (preferably between 30° C. and 60° C.).

The reaction time is generally between a few minutes and a few hours. For the preferred oxadiazinetrione structures, the course of the reaction is easy to follow. The reaction is complete when the evolution of carbon dioxide stops.

The solids contents of the aqueous dispersions formed may vary within wide limits, but are generally between 5 and 70% by weight (preferably between 20 and 60% by weight).

In one preferred embodiment, up to 0.9 equivalents (more preferably up to 0.7 equivalents) of the free isocyanate groups of polyisocyanates (a) are reacted with alcohol (b), after which the remaining isocyanate groups are further reacted with components (c) and (d). If desired, the reaction may also be carried out in such a way that components (c) and (d) are used in less than equivalent quantities, with the residual NCO groups then reacting with, for example, water.

In one particularly preferred embodiment, the free isocyanate groups of the diisocyanatohexyl oxadiazinetrione are urethanized with 0.05 to 1 equivalent of alcohol (b) and the oxadiazinetrione ring, which contains a latent NCO group in the context of the present invention, is opened with cyanamide or neutralized cyanamide.

The reaction products according to the invention have the following properties:

(1) On drying and release of their counterion, the compounds dimerize or oligomerize and lose their ionic character.

(2) The reaction products also lose their dispersing properties in this way. That is, polymers thus dispersed are precipitated.

(3) If the reaction products contain residues of relatively long-chain alcohols (b), they are able to develop hydrophobic character properties.

(4) If the reaction products are used together with the dispersions described, for example, in German Offenlegungsschrift 4,133,572, and contain cyanamide as hydrophilicizing groups, they act as crosslinking agents.

The reaction products according to the invention are suitable for the following applications: (i) softening and optionally hydrophobicizing retanning of leather; (ii)

impregnation of textiles for the wash-resistant improvement of feel and appearance and printing of textiles; (iii) reinforcement of the hydrophobicizing effect of hydrophobicizing substances, such as paraffin; (iv) use as a dispersion stabilizer for textile and leather auxiliaries; (v) use as an emulsifier for cellulose esters (such as nitro-cellulose and cellulose acetobutyrate), PVC, polyvinyl acetate, polyamide, polyurethane, polyethylene, polypropylene, and mixtures thereof when used, for example, as surface treatment preparations for hard parts (e.g., ABS or PVC) or soft substrates (e.g., leather, textiles, or paper).

The reaction products according to the invention are normally used in quantities of 1 to 500% by weight (preferably 20 to 200% by weight), based on the solids both in the reaction products used and in the substrate.

If the reaction products according to the invention are used as emulsifiers for polymers that are dispersed in water-immiscible solvents, they may be used in quantities of 5 to 100% by weight (solid reaction product) based on the solution of the polymer.

If the reaction products according to the invention are only to be used as emulsion promoters, it is generally sufficient to use them in quantities of 1 to 20% by weight (preferably 3 to 10% by weight) (solid reaction product) based on the dispersion to be emulsified.

The mixtures containing the reaction products according to the invention may readily be converted into a dispersion (by stirring or by pouring into the liquor to be applied). For retanning of leather, they are generally poured into the retanning liquor, the dispersion being taken up by the rotating movement of the vat or the tanning machines. The pH value of the retanning liquor or the leather should be above 3 (preferably above 5). Synthetic tanning agents, polymer tanning agents or mineral tanning agents, oiling agents, and dyes may, of course, also be added. The products may be selectively dimerized or oligomerized by addition of acid.

For surface treatment, the dispersion is directly applied to the surface to be treated by spraying, casting, printing, or knife coating. For the reversal process, the dispersion is first applied to a temporary support, one or more further layers are optionally applied, the substrate to be laminated is applied thereto, and the whole is removed from the temporary support.

For textiles, the reaction products according to the invention may be applied not only by the processes mentioned above but also (and preferably) by padding.

Accordingly, the present invention also relates to the use of the reaction products according to the invention for the retanning of leather, as a sizing agent for paper, as a finish for leather and textiles, and as an emulsifier.

The following examples further illustrate details for the preparation and use of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all percentages are percentages by weight.

EXAMPLES

Example 1

186.4 g (1 mol) of lauryl alcohol and 22 g (1 mol) of isophorone diisocyanate were stirred for 6 hours at 60° C. in a one-liter three-necked flask. The reaction mixture had an isocyanate content of 10.28%.

42 g (1 mol) of cyanamide were introduced into the reaction mixture, which was then stirred for 30 minutes. 101.2 g (1 mol) of triethylamine were introduced in portions at 60° C. After being stirred for 1 hour, the mixture was poured into a flat mold, where it solidified at room temperature into a glass-like material that was readily soluble in water.

Example 2

373 g (2 mol) of lauryl alcohol and 444 g (2 mol) of isophorone diisocyanate were stirred at 60° C. in a one-liter three-necked flask. After 6 hours, the reaction mixture had an isocyanate content of 10.36%.

The reaction product was poured slowly with stirring at room temperature into a solution of 82 g (2 mol) of cyanamide and 202.2 g (1.96 mol) of triethylamine in 490 g of water. A slightly opaque solution that was obtained was adjusted to a solids content of 46% by addition of another 400 g of water.

Example 3

380.6 g (2.04 mol) of lauryl alcohol and 932.4 g (4.20 mol) of isophorone diisocyanate were stirred for 4 hours at 70° C. in a one-liter three-necked flask. The mixture had an isocyanate content of 20%.

The reaction product was poured slowly into a solution of 252 g (6 mol) of cyanamide and 607 g (6 mol) of triethylamine in 3,250 g of water. An aqueous solution having a solids content of 39% was obtained.

Example 4

402 g (1.5 mol) of 9-octadecen-1-ol and 315 g (0.75 mol) of 3,5-bis-(6-isocyanatohexyl)-2,4,6-trioxotetrahydro-1,3,5-oxadiazine (technical product, molecular weight 200) were stirred at 90° C in a one-liter three-necked flask.

After 5 hours, the reaction mixture was free from isocyanate. 63 g of a 50% aqueous cyanamide solution (0.75 mol) and 77.3 g of triethylamine were slowly added dropwise at 50° C. After the addition was completed, the mixture was stirred for 2 hours at 50° C.

Example 5

The procedure of Example 3 was repeated with the following changes: 1 mol of oleyl alcohol, 1 mol of 3,5-bis-(6-isocyanatohexyl)-2,4,6-trioxotetrahydro-1,3,5-oxadiazine, 1.35 mol of triethylamine, and 1.5 mol of cyanamide. A 30.6% aqueous dispersion was obtained.

Example 6

611.5 g of a biuretized hexamethylene diisocyanate (Desmodur N 3200, a product of Bayer AG) and 248.7 g of oleyl alcohol were stirred for 4 hours at 60° C. in a one-liter three-necked flask. The reaction product had an isocyanate content of 10.74%.

790 g of the reaction product were slowly stirred into a solution of 83.3 g of cyanamide and 200.7 g of triethylamine in 1,000 g of water. An aqueous solution with a solids content of about 50% was obtained.

Example 7

Example 7 corresponds to Example 1 of German Offenlegungsschrift 3,813,840 (counterpart of U.S. Pat. No. 5,284,928, which is incorporated by reference).

1,000 g of a hexanediol/neopentyl glycol mixed adipate (OH value 65) were reacted with 2,155 g of a biuretized hexamethylene diisocyanate (Desmodur N 3200, a product of Bayer AG) in a five-liter face-ground jar (NCO 14%).

2,450 g of this prepolymer were added dropwise with stirring to a solution of 345 g of cyanamide and 730 g of N,N-dimethyl ethanolamine in 1,500 g of water. A dispersion having a solids content of 70% was obtained.

Example 8

571.2 g of hexamethylene diisocyanate (Desmodur H, a product of Bayer AG), 134 g of trimethylolpropane, and 348.2 g of oleyl alcohol are stirred for 6 h at 80° C. in a 1.5-liter three-necked flask. The resultant prepolymer had an isocyanate content of 10%. 800 g of the isocyanate prepolymer were slowly introduced into a solution of 80 g of cyanamide and 192.8 g of triethylamine in 2,100 g of water. An aqueous solution with a solids content of approximately 34% was obtained.

Example 9

888 g of hexamethylene diisocyanate (Desmodur H, a product of Bayer AG), 104 g of trimethylolpropane, 442.3 g of a dimethylol polydimethylsiloxane with a hydroxyl group content of around 6% (Baysilon OF-OH, a product of Bayer AG), and 565 g of oleyl alcohol were stirred for 5 hours at 90° C. in a two-liter three-necked flask. The prepolymer obtained had an isocyanate content of 9.1%. 1,000 g of the isocyanate prepolymer were slowly stirred into a solution of 85.6 g of cyanamide and 185.6 g of triethylamine in 1,270 g of water. An aqueous solution having a solids content of around 50% was obtained.

Application Example 1

Use In the Retanning of Leather

100% of water (based on shaved weight of the leather all the following percentages are based thereon) were added to a piece of wet blue (size approx. DIN A 5) in a tanning bottle, after which the pH was adjusted to 4.9 by addition of 1% of sodium formate and 0.2% of sodium bicarbonate (running time 1 hour). 11 g (3% of active substance, based on wet blue) of the product of Example 5 were then added and the process was left running for 5 hour. The liquor was fully exhausted, the pH value remaining constant at 4.8. A soft full leather was obtained on drying.

The products of Example 1 to 4 were used with equally good results. Conventional oiling agents and retanning agents could also be used if the pH value of the leather or rather the liquor was above 4.

Application Example 2

Use as a Hydrophobicizing and Softening Agent For Leather

150 Parts of the product of Example 5 were homogeneously emulsified with 22.5 parts of diisopropyl naphthalene and 22.5 parts of a technical $C_{14-17}$ paraffin and 50 parts of $C_{20-27}$ paraffin. A 37% aqueous dispersion was formed.

100 kg of chrome-tanned hides (pared thickness 1.7 mm) were washed for 10 minutes with 200% of water in accordance with Bayer-Anwendungsvorschrift G 903. The hides were then treated for 40 minutes with 50% of water (40° C.) and 2% of TANIGAN PF-N (neutralizing retanning agent of Bayer AG, Leverkusen), a pH value of 4.7 being established. (Although the hides would then normally have been dyed with 4% of dye, this was not done for this Example.) 3% of BAYTIGAN AR (a retanning agent of 40% aqueous polyacrylic acid of Bayer AG which had been diluted beforehand with three times the quantity of water) was added. After 20 minutes, a mixture of 2% of CORIPOL BZN (an oiling agent of Stockhausen GmbH, Krefeld) and 98% of the mixture according to the invention prepared as described immediately above diluted with 4 times the quantity of water was introduced and the process was allowed to run for another 20 minutes. 2% of TANIGAN OS (synthetic substitute tanning agent, Bayer AG, Leverkusen) and 3% of sweet chestnut were then added and, after 90 minutes, the liquor (pH value 4.8) was drained off and the treated hide was washed with 200% of water at 50° C. Most of the mixture prepared as described above (5% in 50% of water at 60° C.) was then added and, after 75 minutes, the liquor was drained off. The leather was then washed once more with 200% of water (50° C.) for 10 minutes, removed, hoarded up overnight, stretched, dried in vacuo, and, finally, hung to dry. The leathers were then staked and ironed for 30 seconds using a vacuum pump. The leathers were soft and hydrophobic (i.e., water sprayed on the leathers ran off in beads).

Application Example 2.1

Use Of the Self-Inhibiting Emulsifiers as Leather Oiling Preparations

The product prepared in Example 6 was emulsified with castor oil in a ratio of 1:1 with the assistance of 0.5% of ammonia. The resulting emulsion was then used on wet blue. 150 g of chrome-tanned leather were placed in 100% of water at 40° C. The process was allowed to run for 1 hour in a bottle containing 1% of sodium formate and 0.2% of sodium bicarbonate until the pH value settled at 4.6. The liquor was discarded and 2.5% (dry matter) of the mixture of emulsifier and castor oil was introduced into fresh liquor of 100% water (50° C). The process was allowed to run for 2 hours. The final pH was 6.0. The leather was then briefly washed, dried, and staked for evaluation. The leather thus treated was soft and showed a distinct oiling effect. Similar tests were carried out with sunflower oil, rapeseed oil, and beef tallow, all of which gave a soft oiled leather as a result of the treatment with the self-inhibiting emulsifier together with the fatty component.

Application Example 2.2

Comparison With the Prior Art

Following the procedure of Application Example 2, 150 parts of the product of Example 7 were emulsified with 22.5 parts of diisopropyl naphthalene and 22.5 parts of $C_{14-17}$ paraffin and 50 parts of $C_{20-27}$ paraffin.

This emulsion was allowed to stand for 24 hours at room temperature. In contrast to the emulsion of Application Example 2 of the invention, the emulsion separated and developed hardly any effect in the retanning/hydrophobicizing process.

Application Example 3

Use as a dispersant For Cellulose Acetobutyrate as a Finish For Leather 70 g of cellulose acetobutyrate were dissolved while stirring in 340 g of iso-octyl acetate and 189 g of butyl acetate. 35 Parts of plasticizer (based on dibutyl phthalate) and 3 parts of an emulsifier based on sulfosuccinate (Sultafon® W 17210, a product of Stockhausen GmbH, Krefeld) were then added.

2 g of the product prepared in Example 3 and 45 g of water were introduced into 100 g of the solution. An emulsion that was stable when stored for several months was obtained and, even if it should separate, could readily be homogenized by shaking.

To prepare this emulsion for use, it was diluted with water in a ratio of 1:1 and stirred with a low-speed stirrer or by hand with a stirring rod.

The emulsion was sprayed onto a primed leather and compared in appearance with a commercial cellulose acetobutyrate emulsion (EUSIN® Emulsion EG, a product of Bayer AG, Leverkusen). Both samples withstood 20,000 wet flexings in a Bally Flexometer (DIN 53351) without damage. The finish according to the invention withstood 200,000 flexings in the dry state, whereas the finish according to the prior art was slightly damaged.

Application Example 4

Use as a Sizing Agent For Paper 6.66 g of a filter paper (measuring 24×24 cm) were treated in a sizing press with the product produced in Example 6 (wet uptake 68%). After drying at 100° C., a Cobb value of 81 was measured.

Application Example 4.1

100 g of the product produced in Example 6 were mixed while stirring with 50 g of molten paraffin (Paraffin P 144, a product of Wintershall, Düsseldorf), 25 g of hot water (approx. 80° C.) were added, and the mixture was cooled while stirring. A 57% stable aqueous dispersion was formed.

6.7 g of paper were treated in the sizing press with the creamy emulsion prepared as described above diluted with water in a ratio of 1:1. Wet uptake was 76%. A sized paper with a Cobb value of 20.7 was obtained after drying at 100° C. Application Example 5

250 g of the dispersant according to Example 9, 592 g of water, 5 g of ammonia water, and 3 g of bentonite were added in a dissolver to 150 g of a copper phthalocyanine blue (Paliogenblau D 7080, a product of BASF, Ludwigshafen). After being stirred for 20 minutes, the product was ground in a bead mill. A blue pigment paste was obtained.

Application Example 5.1

10 g of the pigment dispersion of Application Example 5 were added to 100 g of the polyurethane dispersion according to Example 1 of German Offenlegungsschrift 4,133,572.

Thickener was then added, steps being taken to ensure that the pH value of the mixture did not fall below 5. The mixture was then printed onto a cotton fabric and heated at 150° C.

Immediately after drying, the textile print obtained could be scrubbed 50 times with a wet brush without damage.

Application Example 6

A cotton fabric was treated in a padding machine with 100% wet uptake of the product produced in accordance with Example 8 (from a 30 g/l solution). The fabric was then dried for 3 minutes at 120° C. and for 5 minutes at 150° C.

The fabric thus finished had a full, oily feel which was still noticeable even after washing three times at 40° C.

What is claimed is:

1. A reaction product of (a) an organic polyisocyanate, (b) 0.005 to 0.9 equivalents of a $C_{6-24}$ alcohol per equivalent of NCO or latent NCO present in component (a), (c) 0.1 to 0.995 mol of cyanamide per equivalent of NCO or latent NCO present in component (a), and (d) ammonia or a volatile amine as neutralizing agent for the cyanamide groups of component (c), with the proviso that the reaction product is free from polyester and polyether groups and from halogen atoms.

2. A reaction product according to claim 1 wherein component (b) is a $C_{12-18}$ alcohol.

3. A reaction product according to claim 1 wherein component (a) is a diisocyanate corresponding to formula (III) and/or formula (IV):

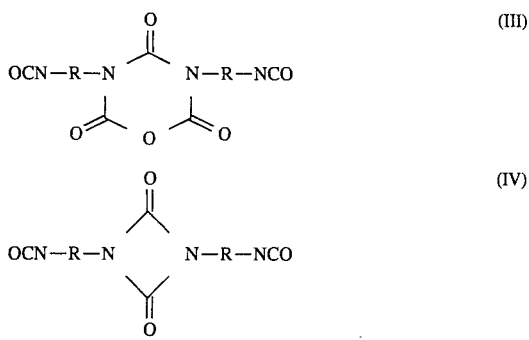

in which each R independently represents the difunctional radical of an aliphatic hydrocarbon containing 1 to 15 carbon atoms, a cycloaliphatic hydrocarbon containing 3 to 15 carbon atoms, an araliphatic hydrocarbon containing 7 to 15 carbon atoms, or an aromatic hydrocarbon containing to 12 carbon atoms.

4. A reaction product according to claim 1 wherein component (a) is 3,5-bis-(6-isocyanatohexyl)-2,4,6-trioxotetrahydro-1,3,5-oxadiazine.

5. A process for the preparation of a reaction product of claim comprising reacting (a) an organic polyisocyanate, (b) 0.005 to 0.9 equivalents of a $C_{6-24}$ alcohol per equivalent of NCO or latent NCO present in component (a), (c) 0.1 to 0.995 mol of cyanamide per equivalent of NCO or latent NCO present in component (a), and (d) ammonia or a volatile amine as neutralizing agent for the cyanamide groups of component (c), with the proviso that components (a) to (d) do not introduce polyester or polyether groups or halogen atoms into the reaction product.

* * * * *